(12) United States Patent
Cory et al.

(10) Patent No.: US 6,609,018 B2
(45) Date of Patent: Aug. 19, 2003

(54) ELECTRODE ARRAY AND SENSOR ATTACHMENT SYSTEM FOR NONINVASIVE NERVE LOCATION AND IMAGING DEVICE

(75) Inventors: Philip C. Cory, Bozeman, MT (US); Joan M. Cory, Bozeman, MT (US)

(73) Assignee: CKM Diagnostics, Inc., Bozeman, MT (US)

(*) Notice: Subject to any disclaimer, the term of this patent is extended or adjusted under 35 U.S.C. 154(b) by 0 days.

(21) Appl. No.: 09/912,535

(22) Filed: Jul. 26, 2001

(65) Prior Publication Data

US 2002/0095080 A1 Jul. 18, 2002

Related U.S. Application Data

(63) Continuation-in-part of application No. 09/624,397, filed on Jul. 27, 2000.

(51) Int. Cl.[7] ................................................. A61B 5/04
(52) U.S. Cl. ........................................ 600/393; 600/372
(58) Field of Search ................................ 600/393, 382, 600/372, 375, 384, 386, 391, 394, 395

(56) References Cited

U.S. PATENT DOCUMENTS

| | | |
|---|---|---|
| 2,008,295 A | 7/1935 | Smith |
| 2,018,080 A | 10/1935 | Martienssen |
| 2,298,506 A | 10/1942 | Parker et al. |
| 2,704,064 A | 3/1955 | Fizzell et al. |
| 3,078,850 A | 2/1963 | Schein et al. |
| 3,612,060 A | 10/1971 | Colyer |
| 3,612,061 A | 10/1971 | Collins |
| 3,624,484 A | 11/1971 | Colyer |
| 3,664,329 A | 5/1972 | Naylor |
| 3,682,162 A | 8/1972 | Colyer |
| 3,830,226 A | 8/1974 | Staub et al. |
| 3,954,100 A | 5/1976 | Sem-Jacobsen |
| 3,989,051 A | 11/1976 | Nozhnikov et al. |
| 4,016,870 A | 4/1977 | Lock ................... 128/21.1 C |

(List continued on next page.)

FOREIGN PATENT DOCUMENTS

| | | | |
|---|---|---|---|
| WO | WO 00/41618 | 7/2000 | |
| WO | WO 02/09584 | * 2/2002 | ............ A61B/5/05 |

OTHER PUBLICATIONS

Arthur L. Kaslow, et al., "Dragon Chasing: A New Technique for Acupuncture Point Finding and Stimulation", American Journal Acupuncture, vol. 3, No. 2, Apr.–Jun. 1975.

Kerjariwal et al., "Development of a Device for Non–Invasive Nerve Location", Abstracts, 8th World Congress on Pain, Vancouver, British Columbia, Canada, Aug. 17–22, 1996.

G. Kwok et al., "Mapping Acupuncture Points Using Multi Channel Device", Australasian Physical and Engineering Sciences in Medicine, vol. 21, No. 2, 1998.

(List continued on next page.)

Primary Examiner—Roy D. Gibson
Assistant Examiner—Peter J Vrettakos
(74) Attorney, Agent, or Firm—McDermott, Will & Emery (57) ABSTRACT

A system for detecting and marking the positions of peripheral nerves is disclosed. A disposable or reusable electrode array comprising a plurality of electrodes is combined with a disposable sensor attachment system comprising conductor islands. In use, the electrode array is connected to a peripheral nerve detection instrument. The disposable sensor attachment system is attached to an electrode sensor region. The sensor attachment system is then adhered to an area of skin, detection is carried out, and then the electrode array is peeled back from the skin, leaving a skin marking guide in place. The skin marking guide is then used to mark areas of interest to a therapist.

18 Claims, 9 Drawing Sheets

U.S. PATENT DOCUMENTS

| | | | |
|---|---|---|---|
| 4,157,087 A | 6/1979 | Miller et al. | |
| 4,257,424 A | 3/1981 | Cartmell | |
| 4,334,542 A | 6/1982 | Takinishi et al. | |
| 4,370,984 A | 2/1983 | Cartmell | |
| 4,390,023 A | 6/1983 | Rise | |
| 4,408,617 A | 10/1983 | Auguste | |
| 4,459,995 A | 7/1984 | Conners et al. | |
| 4,461,304 A | 7/1984 | Kuperstein | |
| 4,486,835 A | 12/1984 | Bai et al. | |
| 4,515,168 A | 5/1985 | Chester et al. | |
| 4,539,640 A | 9/1985 | Fry et al. | |
| 4,540,002 A | 9/1985 | Atlas | |
| 4,557,271 A | 12/1985 | Stoller et al. | |
| 4,578,635 A | 3/1986 | Mee et al. | |
| 4,595,013 A | 6/1986 | Jones et al. | |
| 4,616,660 A | 10/1986 | Johns | |
| 4,619,266 A | 10/1986 | Hodgson | |
| 4,630,615 A | 12/1986 | Yomtov | |
| 4,633,889 A | 1/1987 | Talalla et al. | |
| 4,635,641 A | 1/1987 | Hoffman | |
| 4,649,932 A | 3/1987 | Smith | |
| 4,685,467 A | 8/1987 | Cartmell et al. | |
| 4,702,259 A | 10/1987 | Ferreira et al. | |
| 4,753,246 A | 6/1988 | Freeman | |
| 4,763,660 A | 8/1988 | Kroll et al. | |
| 4,794,934 A | 1/1989 | Motoyama et al. | |
| 4,805,621 A | 2/1989 | Heinze et al. | |
| 4,807,638 A | 2/1989 | Sramek | |
| 4,823,797 A | 4/1989 | Heinze et al. | |
| 4,836,214 A | 6/1989 | Sramek | |
| 4,838,273 A | 6/1989 | Cartmell | |
| 4,892,105 A | 1/1990 | Prass | |
| 4,917,093 A | 4/1990 | Dufresne et al. | |
| 4,926,865 A | 5/1990 | Oman | |
| 4,962,766 A | 10/1990 | Herzon | |
| 4,969,468 A * | 11/1990 | Byers et al. | 600/373 |
| 5,010,896 A | 4/1991 | Westbrook | |
| 5,044,368 A | 9/1991 | Putz | |
| 5,058,605 A | 10/1991 | Slovak | |
| 5,063,937 A | 11/1991 | Ezenwa et al. | |
| 5,067,953 A | 11/1991 | Feucht | |
| 5,092,332 A | 3/1992 | Lee et al. | |
| 5,092,344 A | 3/1992 | Lee | |
| 5,150,708 A | 9/1992 | Brooks | |
| 5,199,432 A | 4/1993 | Quedens et al. | |
| 5,203,344 A | 4/1993 | Scheltinga et al. | |
| 5,215,100 A | 6/1993 | Spitz et al. | |
| 5,272,624 A | 12/1993 | Gisser et al. | |
| 5,284,153 A | 2/1994 | Raymond et al. | |
| 5,284,154 A | 2/1994 | Raymond et al. | |
| 5,295,482 A | 3/1994 | Clare et al. | |
| 5,305,746 A | 4/1994 | Fendrock | |
| 5,335,668 A | 8/1994 | Nardella | |
| 5,353,802 A | 10/1994 | Ollmar | |
| 5,356,428 A | 10/1994 | Way | |
| 5,361,762 A | 11/1994 | Gunter | |
| 5,366,497 A | 11/1994 | Ilvento et al. | |
| 5,385,150 A | 1/1995 | Ishikawa | |
| 5,388,577 A | 2/1995 | Hubbard | |
| 5,397,344 A | 3/1995 | Garfield et al. | |
| 5,427,098 A | 6/1995 | Faupel et al. | |
| 5,443,486 A | 8/1995 | Hrdlicka et al. | |
| 5,449,378 A | 9/1995 | Schouenborg | |
| 5,501,230 A | 3/1996 | Laribiere | |
| 5,503,157 A | 4/1996 | Sramek | |
| 5,522,877 A | 6/1996 | Garfield et al. | |
| 5,529,072 A | 6/1996 | Sramek | |
| 5,534,003 A | 7/1996 | Cole | |
| 5,560,372 A * | 10/1996 | Cory | 600/554 |
| 5,563,067 A | 10/1996 | Sugihara et al. | |
| 5,626,575 A | 5/1997 | Crenner | |
| 5,642,734 A | 7/1997 | Ruben et al. | |
| 5,645,063 A | 7/1997 | Straka, Jr. | |
| 5,715,821 A | 2/1998 | Faupel | |
| 5,720,296 A | 2/1998 | Cha | |
| 5,733,151 A | 3/1998 | Edsall et al. | |
| 5,772,591 A | 6/1998 | Cram | |
| 5,775,331 A | 7/1998 | Raymond et al. | |
| 5,779,642 A | 7/1998 | Nightengale | |
| 5,782,238 A | 7/1998 | Beitler | |
| 5,797,854 A | 8/1998 | Hedgecock | |
| 5,800,350 A | 9/1998 | Coppleson et al. | |
| 5,830,151 A | 11/1998 | Hadzic | |
| 5,830,175 A | 11/1998 | Flower | |
| 5,848,966 A | 12/1998 | Gusakov et al. | |
| 5,851,191 A | 12/1998 | Gozani | |
| 5,853,373 A | 12/1998 | Griffith et al. | |
| 5,885,219 A | 3/1999 | Nightengale | |
| 5,897,505 A | 4/1999 | Feinberg et al. | 600/547 |
| 5,904,712 A | 5/1999 | Axelgaard | |
| 5,916,157 A | 6/1999 | Crosz, Jr. | |
| 5,916,159 A | 6/1999 | Kelly et al. | |
| 5,916,179 A | 6/1999 | Sharrock | |
| 5,928,158 A | 7/1999 | Aristides | |
| 5,957,860 A | 9/1999 | Rodiera Olive | |
| 5,961,484 A | 10/1999 | Gusakov et al. | |
| 5,976,094 A | 11/1999 | Gozani | |
| 5,984,102 A | 11/1999 | Tay | |
| 5,991,649 A | 11/1999 | Garfield et al. | |
| 6,023,631 A | 2/2000 | Cartmell et al. | |
| 6,032,063 A * | 2/2000 | Hoar et al. | 600/372 |
| 6,032,064 A * | 2/2000 | Devlin et al. | 600/383 |
| 6,038,485 A * | 3/2000 | Axelgaard | 607/148 |
| 6,044,294 A | 3/2000 | Mortzavi et al. | |
| 6,047,202 A * | 4/2000 | Finneran et al. | 600/382 |
| 6,051,422 A | 4/2000 | Kovacs et al. | |
| 6,055,448 A | 4/2000 | Anderson et al. | |
| 6,055,452 A | 4/2000 | Pearlman | |
| 6,090,545 A | 7/2000 | Wohlstadter et al. | |
| 6,115,623 A | 9/2000 | McFee | |
| 6,122,544 A | 9/2000 | Organ | |
| 6,132,386 A | 10/2000 | Gozani et al. | |
| 6,132,387 A | 10/2000 | Gozani et al. | |
| 6,146,335 A | 11/2000 | Gozani | |
| 6,157,851 A | 12/2000 | Kelly et al. | |
| 6,173,198 B1 | 1/2001 | Schulze et al. | |
| 6,295,463 B1 | 9/2001 | Stenzler | |
| 6,360,119 B1 * | 3/2002 | Roberts | 600/509 |

OTHER PUBLICATIONS

G. Kwok et al., Mapping Acupuncture Points Using Multi Channel Device, *Australasian Physical & Engineering Sciences in Medicine*, 21(2):68–72, 1998.

David T. Lykken, Square–Wave Analysis of Skin Impedance, *Psychophysiology*, 7(2):262–275, 1971.

Maria Reichmanis et al., Electrical Correlates of Acupuncture Points, *IEEE Transactions on Biomedical Engineering*, BME 22:533–535, 1975.

J. Jossinet and E. McAdams, Hydrogel Electrodes in Biosignal Recording, *Annual International Conference on the IEEE Engineering in Medicine and Biology Society*, 12(4):1490–1491, 1990.

\* cited by examiner

INPUT CURRENT
(BY ELECTRODE #)

FIG. 10B

OUTPUT VOLTAGE
(BY ELECTRODE #)

ELECTRODE ARRAY AND SENSOR ATTACHMENT SYSTEM FOR NONINVASIVE NERVE LOCATION AND IMAGING DEVICE

CROSS-REFERENCE TO RELATED APPLICATIONS

This application is a Continuation-in-Part of and claims priority from U.S. application Ser. No. 09/624,397, filed Jul. 27, 2000.

TECHNICAL FIELD

This invention relates to a medical device for the noninvasive location and imaging of peripheral nerves. Specifically, the present invention is a sensor system for use at the skin surface comprising an electrode array assembly with one or more electrodes and a sensor attachment system. Each electrode in the electrode array assembly maintains a connection to peripheral nerve detection and imaging instrumentation. One or more return wires are attached to the electrode array assembly and to a skin surface electrode during use of the sensor system. A disposable, sterile sensor attachment system allows conductance between the electrode array and the skin surface of the subject. The sensor attachment system contains individual conductor islands, each adapted to align accurately with a specific electrode of the electrode array. The layer of the sensor attachment system that adheres to the skin surface of the subject may be left on the skin at the end of sampling to provide a skin marking guide. This facilitates the positioning of needles for subsequent nerve stimulation or therapy.

BACKGROUND OF THE INVENTION

The use of direct current skin surface conductance or resistance measurements has been employed in many forms for the identification of peripheral nerves, myofascial trigger points, and acupuncture points (Cory, et al., Characterization of cutaneous electrical hyperconductivity sites associated with myfascial trigger points and tarsal tunnel syndrome. In: *Abstracts, 8th World Congress on Pain* (Seattle: IASP Press, 1996), p. 54; Kaslow A L and Lowenschuss O. Dragon chasing: a new technique for acupuncture point finding and stimulation. *American Journal of Acupunture,* 3(2):157–160, 1975); Kejariwal, et al., Development of a device for non-invasive nerve location. In: *Abstracts, 8th World Congress on Pain* (Seattle: IASP Press, 1996), p.279–280; Kwok, et al., Mapping acupunture points using multi channel device. *Australas Phys Eng Sci Med,* 21(2):68–72, 1998; Lykken, Square-wave analysis of skin impedance. *Psychophysiology,* 7(2):262–275, 1971. An early example of this was the use of a transcutaneous electrical nerve stimulation (TENS) unit to identify acupuncture points. When a TENS unit is coupled between examiner and subject, the finger of the examiner acts as a sampling electrode (Kaslow, et al., Dragon chasing: a new technique for acupuncture point finding and stimulation. *American Journal of Acupunture,* 3(2):157–160, 1975)). However, the literature in the field illustrates inconsistency in locating these sites through electrical conductance measurements (Reichmanis et al., Electrical correlates of acupuncture points. *IEEE Transactions on Biomedical Engineering, BME* 22:533–535, 1975).

U.S. Pat. No. 4,016,870 to Lock describes a system for acupuncture point location in which a single, hand-held probe of undisclosed composition is used to determine sites of high skin surface conductance. U.S. Pat. No. 5,897,505 to Feinberg, et al., describes a system for measuring selective tissue conductance and temperature utilizing chrome-plated, brass electrodes in a handheld embodiment. Although each of these systems measures conductance at the skin surface, they suffer two main drawbacks. First, metallic electrodes display uneven current densities at the skin surface-electrode interface, which is largely dependent on the underlying moisture pattern of the skin. Devices for measuring skin surface conductance and resistance that do not employ aqueous interfaces are particularly subject to this effect and, in some cases, current densities became high enough to produce a painful sensation. Second, handheld devices are subject to uncontrolled application pressures. This is complicated in larger diameter electrode systems, such as that of U.S. Pat. No. 5,897,505 to Feinberg, where the angle of application causes pressure to be unequally distributed on the skin surface. The use of electrical conductance measurements at the skin surface to locate nerve tissue is facilitated by the use of aqueous electrodes, rather than metallic or dry silver—silver chloride electrodes, and by the use of non-sinusoidal, alternating current waveforms. Based upon observations such as these, a device that locates peripheral nerves transcutaneously was disclosed in the commonly owned U.S. Pat. No. 5,560,372 to Cory (the disclosure of which is incorporated herein by reference).

Figure 9:
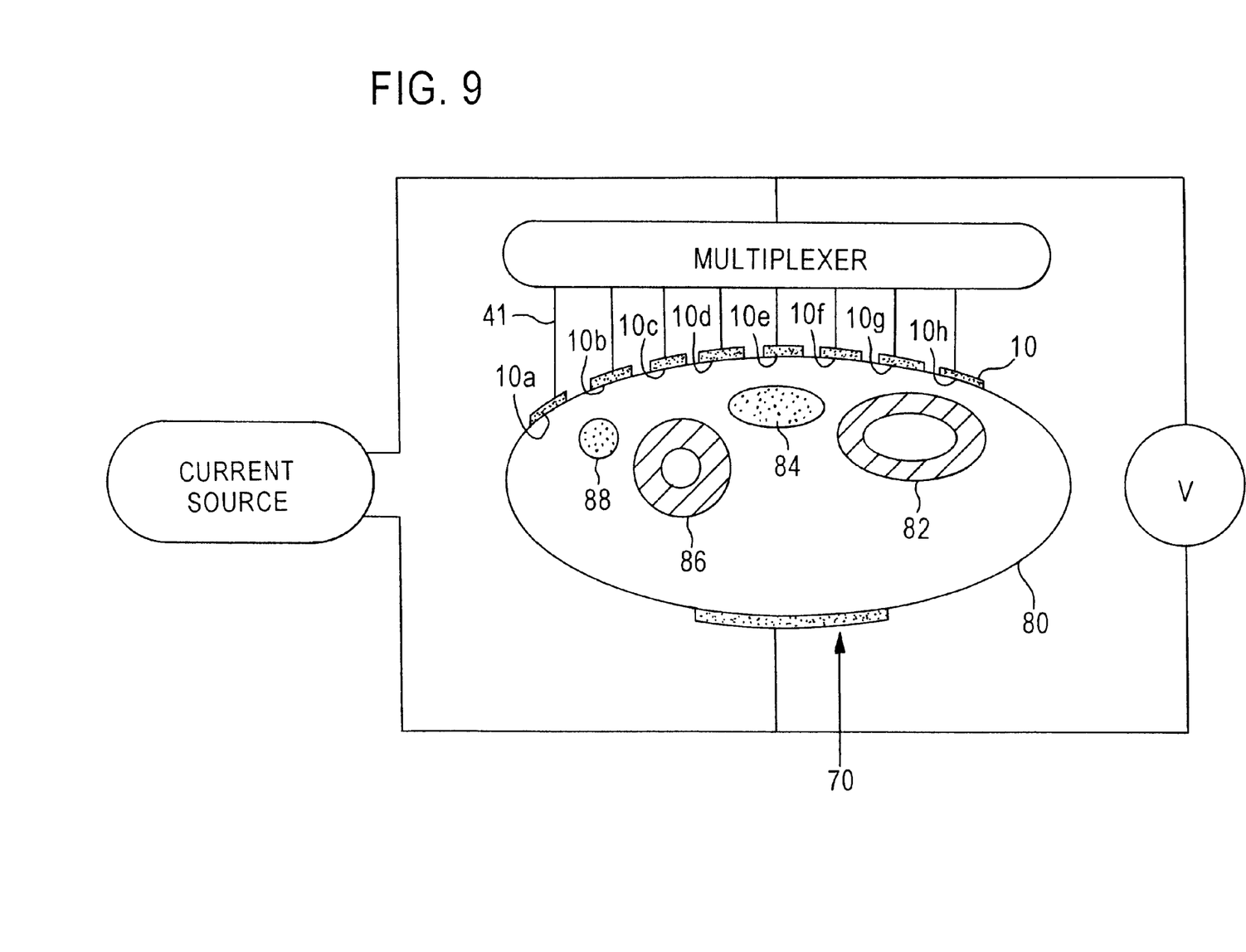
FIG. 9 illustrates a prior art embodiment of an array sensor in a nerve mapping device.

FIG. 9 is a circuit diagram of the non-invasive, peripheral nerve mapping device according to the U.S. Pat. No. 5,560,372 to Cory as it is positioned over the forearm of a patient. The sampling electrode (10) depicted herein comprises eight electrodes (10*a–h*) having leads (41) arranged in a linear array and applied to the volar surface of the forearm on the epidermal surface (80). The reference electrode (70) is placed on the dorsal forearm. A constant current output is applied between the two electrodes (10, 70) on the epidermal surface (80). The voltage difference V between the two electrodes is measured and varies from adjacent skin sites as the electrical conductance of the skin changes. The reference electrode (70) may comprise a conductive carbon impregnated silastic pad provided with an insulated metal foil sheet laminated thereto. The metal foil sheet is in electrical contact with a connector element. The reference electrode may further contain adhesive layer laminated to the bottom of the silastic pad provided with a silicon release sheet attached to the adhesive layer. Reference electrode may comprise a carbon-impregnated silastic pad provided with a layer of pharmaceutical electrode gel placed on the bottom of the pad to be positioned against the skin.

Figure 10A:
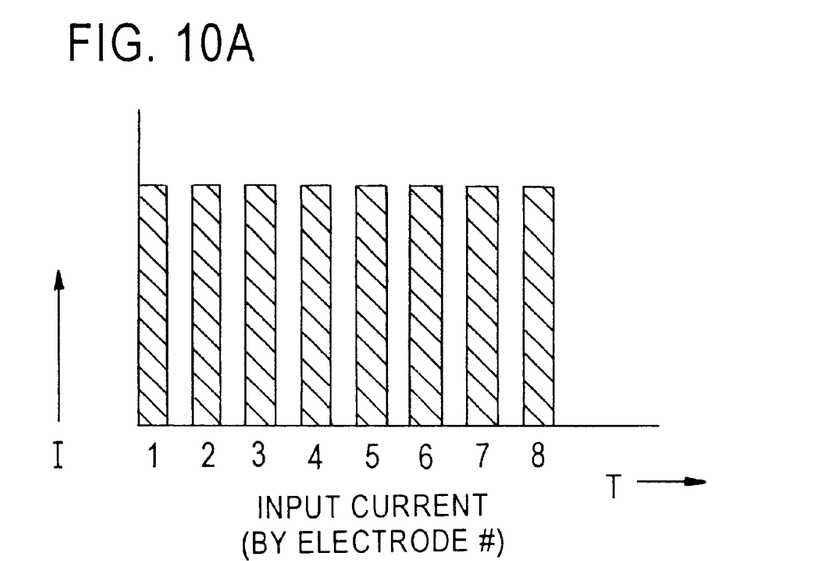
FIGS. 10A and 10B illustrate a prior art operation of an array sensor to sense various types of nerves in a nerve mapping device.
Figure 10B:
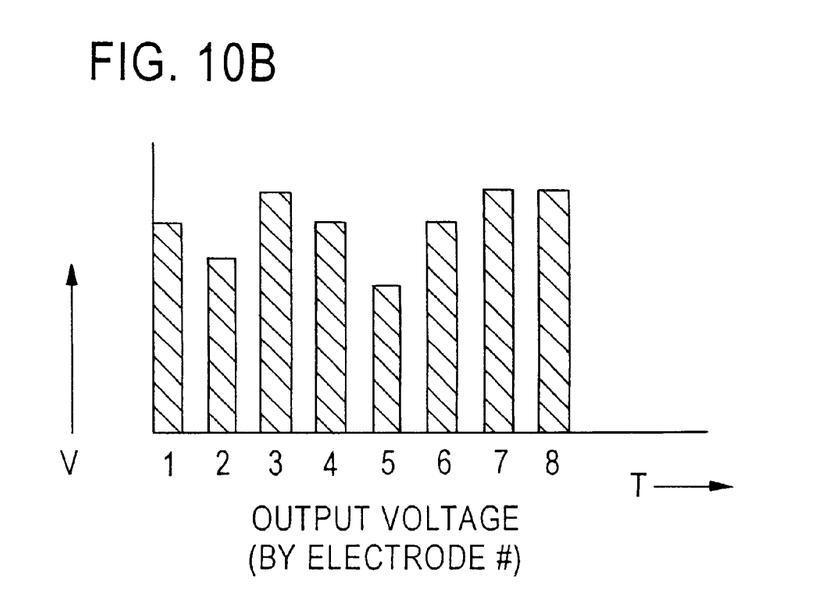

FIG. 10(A) depicts the constant current input (I) for each sub-electrode (10*a* through 10*h*), numbers 1–8 respectively, as shown in FIG. 9. FIG. 10(B) depicts the voltage output V for each sub-electrode. With reference to FIG. 9 and FIG. 10(B), electrode number (10*b*), number 2 in FIG. 10(B) is positioned over ulnar nerve (88). As shown in FIG. 10(B), electrode (10*b*) indicates the position of the ulnar nerve (88) by a decrease in output voltage. Similarly, electrodes (10*d*) and (10*e*), numbers 4 and 5 in FIG. 10(B), display a similar output voltage decrease as they are positioned over median nerve (84). Thus, the non-invasive, peripheral nerve mapping device according to the present invention accurately identifies the location of subcutaneous nerves. Voltage minima (conductance maxima) are observed over the ulnar and median nerves (88, 84) at constant current. Sites of decreased skin voltage differentials are mapped and have been shown by nerve stimulator technique, direct dissection and local anesthetic blockage, in animal and human models, to correspond to the location of subcutaneous nerves.

The problem of avoiding metallic interfaces with the skin surface is addressed by the use of water-saturated felt electrodes in U.S. Pat. No. 5,560,372 to Cory and by the use of hydrogels (Jossinet and McAdams, Hydrogel Electrodes in Biosignal Recording. *Annual International Conference on the IEEE Engineering in Medicine and Biology Society,* 12(4):1490–1491, 1990). The ability to obtain reproducible skin surface conductance and resistance readings allows the recognition of skin surface sites that correspond to underlying peripheral nerves. While this approach circumvents the problems of current density disparities, of the formation of thin oxidation films on the electrodes, and of subsequent back electromotive force, additional problems remain that are associated with the interface between the sampling electrodes and the skin surface.

SUMMARY OF THE INVENTION

It is an object of the present invention to provide a sensor system comprising an electrode array and a sensor attachment system for use with an electrical field generating device that can non-invasively detect peripheral nerves.

It is a further object of the present invention to provide a method for detecting peripheral nerves using the aforementioned sensor system.

It is a further object of the present invention to provide for an electrode array, which is flexible, reusable, and suitable for use, either alone or in combination with a sensor attachment system as herein described.

It is a further object of the present invention to provide for a sensor attachment system, comprising conductor islands, which is disposable and suitable for use in combination with an electrode array as herein described.

Further objects and advantages of the invention will be apparent from the following description of the invention.

In satisfaction of the foregoing objects and advantages, the present invention provides an electrode array comprising:

- a sheet of electrically non-conductive material having a sensor electrode region, an instrumentation connector region and a flexible stem region mechanically joining the electrode sensor region and the instrumentation connector region;
- an electrode array having one or more electrodes, which are disposed within the sensor electrode region,
- a connection lead corresponding to each electrode disposed within the instrumentation connector region,
- a return lead disposed within the instrumentation connector region,
- an electrically conductive connection between each electrode and its corresponding connection lead; and
- features on the sensor electrode region for alignment with a skin attachment system, and for alignment with the image displayed by a nerve location device.

DETAILED DESCRIPTION OF THE INVENTION

The medical device of the present invention is a sensor system that comprises two components. A sensor system of the present invention thus comprises an electrode array and a sensor attachment system to attach to the skin. When combined to form the sensor system, both the electrode array and the sensor attachment system are presented in the form of complementary arrays of electrodes and conductor islands, respectively. The electrode array comprises one or more electrodes, advantageously four or more electrodes. The electrodes may be arranged randomly, in a single line, or in another fixed order.

Advantageously, the electrodes of the array may be arranged in plural rows. The adjacent rows may be in line with one another or offset with respect to their nearest neighbor(s). A preferred arrangement is for the array to comprise a minimum of four electrodes arranged as two or more rows, where adjacent rows are in line with one another. Another preferred arrangement is for the array to comprise a minimum of four electrodes arranged as two or more rows of electrodes, where adjacent rows are offset with respect to one another.

A further preferred arrangement is for there to be a minimum of two rows of four or more electrodes each.

A further preferred arrangement is for there to be a minimum of two rows of eight or more electrodes each.

Another further preferred arrangement is for there to be a minimum of eight rows of eight electrodes each.

Figure 1:
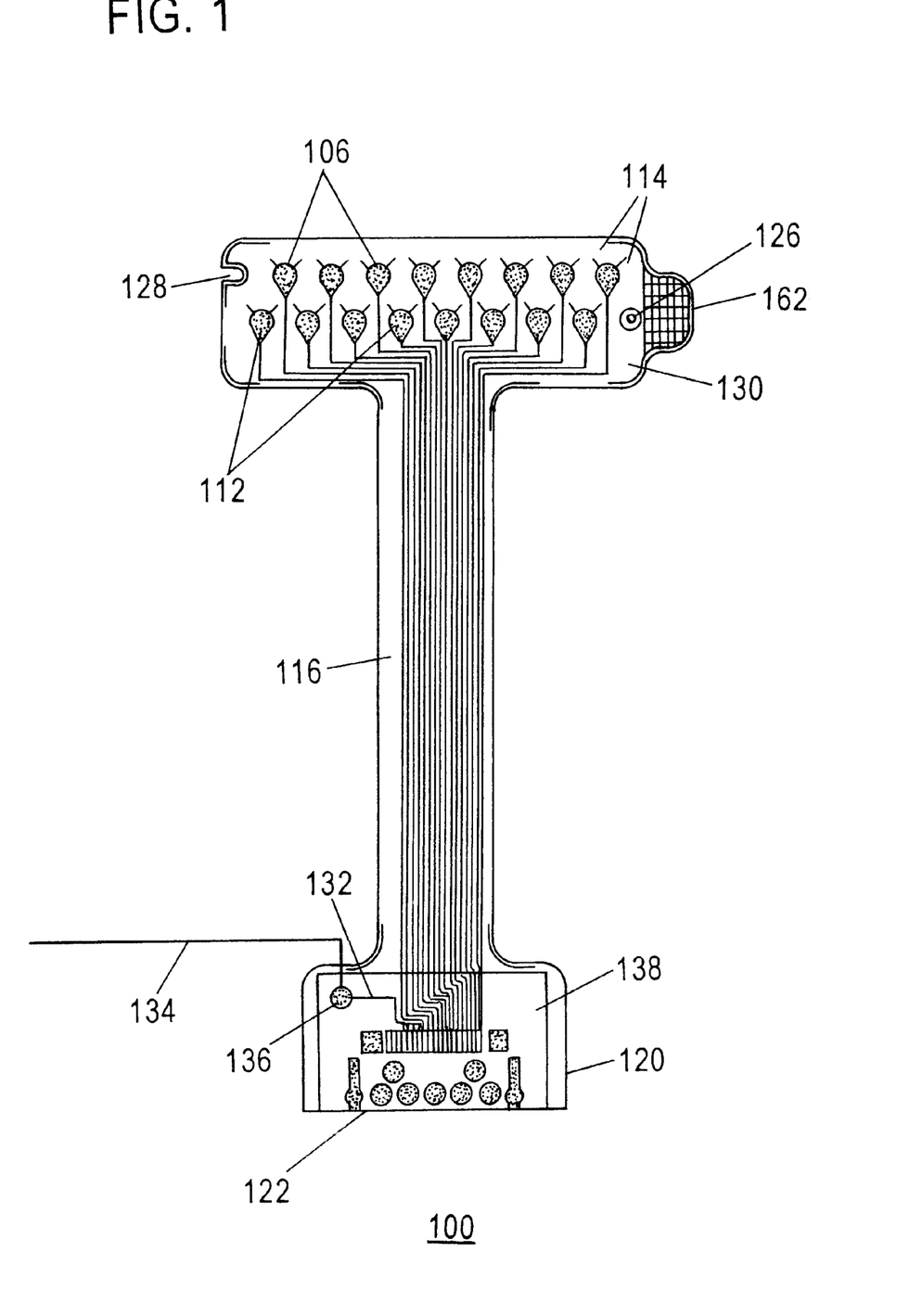
FIG. 1 is a basic depiction of an electrode array of a first embodiment of the present invention in a 16-electrode conformation, view from side not facing skin (top view).
Figure 4:
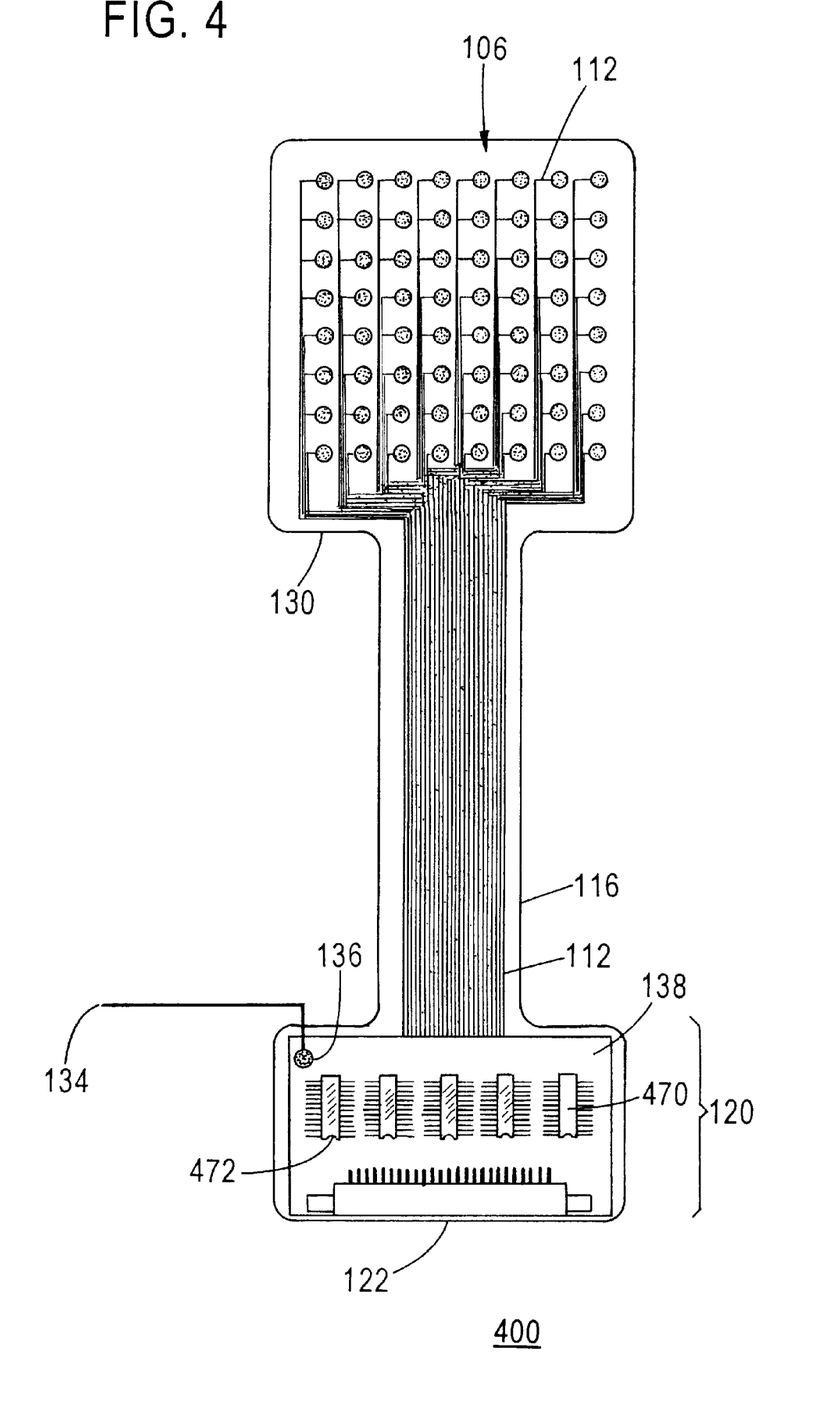
FIG. 4 shows an exemplary electrode array of a second embodiment of the present invention in a 64-electrode conformation, top view.

An exemplary embodiment according to the present invention is a two row array, as depicted in FIG. 1, where an offset arrangement of adjacent rows is used. Another exemplary embodiment according to the present invention is an eight row arrangement, as depicted in FIG. 4, where adjacent rows are in line with one another.

By the foregoing, it should be apparent that any number of conformations is possible with this invention. The important consideration in constructing an electrode array assembly of the present invention is that the electrodes of the electrode array line up with the conductor islands of the sensor attachment system so that they can operate together as the herein described sensor system.

An electrode array assembly of the present invention may advantageously be made flexible so that the electrode array assembly may conform to a wide variety of body surfaces, locations, and circumferences. To achieve this flexibility, the electrode array should comprise as a support structure a flexible, electrically non-conductive sheet. Also, it is useful to employ very thin, narrow, electrically conductive paste or adhesive as an electrical connection between the electrodes in the electrode array region and the leads in the electrical connector region of the electrode array. The electrical connections may also comprise suitably applied metallic ink, metallic wire, or conductive trace.

The electrode array of the present invention may be reused, a feature which is particularly achieved when the electrode array is used with a separate sensor attachment system of the present invention.

The electrode surface should be chemically, as well as biologically, inert. In other words, the electrode surface should not chemically react with, or be degraded by, surfaces which it will contact during normal use. To obtain reproducible measurements, the formation of thin, oxidation films on the electrode surface must be avoided. At the same time, the electrode array must be resistant to damage by bending and twisting. The electrode array must also be stable when cleaned with common sterilizing agents, such as isopropyl alcohol. The electrode array must also be stable upon sterilization by ethylene oxide, gamma radiation, or autoclaving. Suitable materials for the electrode surfaces include gold, gold-plated copper, nickel-plated metal, platinum, palladium, silver—silver chloride or another conductive metal, metal salt combination or conductive polymer(s) such as polyaniline.

In preparing the electrode array assemblies of the present invention, thought must be given to the reduction of sampling error. The present inventors have performed experiments to determine the size parameters that minimize sampling error. The present invention may be advantageously practiced by constructing electrode arrays in which the electrode diameters are in the range of about 2–3 mm, with edge-to-edge spacing of about 3 mm. Smaller electrode diameters and closer electrode spacing may result in excessive variation between sample readings. It is believed that, at smaller electrode diameters, conductor resistance increases due to decreasing cross-sectional area in relation to the electrical field path, which may introduce variation in sample readings. However, where such variations are tolerable, smaller electrode diameters may be used. Of course, larger electrode diameters and spacings may be advantageously employed and are contemplated as being within the scope of the present invention, although smaller diameters are generally preferred due to their generally more favorable resolution characteristics. The ordinary artisan will appreciate that a wide variety of electrode diameters and spacings may be used and are contemplated as being within the scope of the present invention.

The sensor attachment system of the present invention provides an interface between the electrode array and the skin surface of a living being, preferably a mammal, more preferably a human patient. The sensor attachment system comprises a plurality of layers. One layer, hereinafter the support layer, contains a plurality of conductor-islands arranged in a support. The conductor-islands are formed from a suitable conductive material such as a hydrogel, or silver—silver chloride gel. Another layer, hereinafter the skin marking guide layer, is fenestrated (i.e. has holes) so that the conductor islands protrude through the holes therein. The support layer and the skin marking guide layer are held together by an adhesive that is easily broken, so that after imaging the peripheral nerves, the practitioner may then peel the support layer away from the skin marking guide layer, leaving the latter attached to the skin.

The hydrogel or silver—silver chloride gel may be any electrically conductive hydrogel or silver—silver chloride gel known in the medicinal, biofeedback or biological testing arts.

The hydrogel polymers are desirably water interactive and/or hydrophilic in nature and are of a molecular weight or structure, or have been modified such that they absorb significant quantities of water and may form hydrogels when placed in contact with water or aqueous media for a period of time sufficient to reach equilibrium with water, but which do not fully dissolve at equilibrium in water.

The hydrogel polymers include polymers from the group of homo- and copolymers based on various combinations of the following vinyl monomers: acrylic and methacrylic acids, acrylamide, methacrylamide, hydroxyethylacrylate ormethacrylate, vinylpyrrolidones, as well as polyvinylalcohol and its co- and terpolymers, polyvinylacetate, its co- and terpolymers with the above listed monomers and 2-acrylamido-2-methyl-propanesulfonic acid (AMPS®) and sulfonated styrenes. Very useful are copolymers of the above listed monomers with copolymerizable functional monomers such as acryl or methacryl amide acrylate or methacrylate esters where the ester groups are derived from straight or branched chain alkyl, aryl having up to four aromatic rings which may contain alkyl substituents of 1 to 6 carbons.

Most preferably the hydrogels of the invention should be composed of synthetic copolymers from the group of acrylic and methacrylic acids, acrylamide, methacrylamide, hydroxyethylacrylate (HEA) or methacrylate (HEMA), vinylpyrrolidones, and polyacrylonitriles. Specific illustrative examples of useful polymers are the following types of polymers: hydroxyethyl methacrylate, crosslinked polyvinyl alcohol, crosslinked N-vinylpyrrolidone/acrylic acid copolymers, crosslinked poly(N-vinyl lactam), crosslinked polyacrylamide, crosslinked polyacrylic acid, and crosslinked poly(2-acrylamide-2-methylpropane) sulfonic acid, or "Procam" or Hydrogel A11926, tradenames of Ludlow Technical Products hydrogel material.

The foam used in the support layer may be any foam known in the art for such applications. The foam support layer should be flexible so as to conform to the surface to which it is applied. Any type of foam layer may be used but preferred foams are closed cell foams such as polyethylene. Closed cell foams are foams which have generally spherical discrete pores which are not connected. However, equivalent support layers may be used as known in the medical arts.

The skin marking guide layer may be made of any polymeric material known in the medical arts. Particularly advantageous are those polymeric materials that are clear or translucent. Polyurethane, polypropylene, polyvinyl chloride, and copolymers thereof, all of which are known in the art, are preferred. The polymeric materials may be colored in order to enhance their visibility against skin. Particularly preferred are bright colors that offer enhanced contrast on any colored skin. Color such as blue and white are particularly preferred for the skin marking guide, however other colors, such a fluorescent yellow, orange, green and magenta may also be used.

The nerve imaging instrument to be employed is not critical to the present invention and may be any suitable instrument known in the art, such as the multiplexed system disclosed in commonly owned U.S. Pat. No. 5,560,372 to Cory, incorporated herein by reference.

The following non-limiting advantages may be realized by practicing this invention:

1. Sterility. The new sensor attachment system directly contacts the skin of the subject and should be a sterile, disposable, adhesive patch. The electrode array, to which the sensor attachment system operatively attaches to the skin, may extend about six inches away from the skin of the subject, may be disposable or may be reusable and cleansed with isopropyl alcohol or sterilized under ethylene oxide, gamma radiation, or autoclaving.
2. Skin marking. Once samples have been taken with the sensor, all but the bottom (skin marking guide) layer of the sensor attachment system may be removed from the skin of the subject. This bottom layer is fenestrated, with holes that correspond to the location of the electrodes in the electrode array, and provides a skin marking guide. Skin can be marked through this skin marking guide to facilitate subsequent injection(s) at the site(s) chosen by the practitioner based upon the readings obtained, or the skin marking guide may be left in place on the skin to provide a convenient template for guiding a nerve stimulation needle or other needle.
3. Pressure applied to electrodes. The electrode array and sensor attachment system, joined together, are placed on the skin surface before sampling. The joined devices are held on the skin by virtue of an adhesive on the sensor attachment system. This arrangement was designed in part to circumvent the possibility that unequal pressures applied to each of the electrodes by the practitioner would interfere with the readings obtained at sampling.
4. Motion artifacts. Stable adherence of the sensor attachment system to the skin of the subject and to the electrode array decreases the possibility of motion artifacts.
5. Quality of image. The number of electrodes in the electrode array assembly may be increased in order to improve the resolution possible with the device.
6. Flexibility. The sensor attachment system and electrode array may be manufactured with different numbers of electrodes in different arrangements to address multiple uses and user preferences.
7. Imaging of a two-dimensional area. To image a two-dimensional area, as required for neurodiagnostic applications of the device, the sensor attachment system and electrode array may be manufactured in a two-dimensional rather than a linear format (for example, an 8×8 array). This circumvents the need to move the device along a line on the skin surface, which is cumbersome for the operator and subject to inaccuracy.
8. Parts replacement. The sensor attachment system is disposable after each use, but is designed as a sterile part that is inexpensive to produce. The electrode arrays may be designed as reusable parts, but would be subject to wear and tear during use and sterilization. This invention has the practical advantage of separating the electrode array from the reminder of the device so that the electrode arrays, if nondisposable, may easily be replaced at minimal cost.
9. Operator's hands. The new invention offers an important practical advantage in freeing up the hands of the practitioner while samples are taken and displayed.
10. Acceptability in practice. The new invention significantly decreases the steps required to sample the skin surface, reducing the time required for nerve localization.
11. Size. The bulk of the device that is in proximity to the subject has been reduced significantly by this invention, facilitating use of the device and acceptance by the subject.
12. Placement of the return electrode(s). The attachment of the return electrode wire(s) of limited length to the electrode array minimizes errors in the placement of the return electrode(s).

Further uses, benefits and features of the present invention will be seen from a review of the detailed description of the preferred embodiments in conjunction with the various figures of the drawings.

Preferred Embodiments

An exemplary electrode array 100 according to the present invention is depicted in FIG. 1. The electrode array 100 has 16 electrodes 106, arranged in two rows, which are offset with respect to one another. Another electrode array 400 is depicted in FIG. 4. Electrode array 400 has 64 electrodes 106, arranged in eight rows and eight columns. Surfaces (not shown) of electrodes 106 are exposed through a non-conductive sheet (not shown) facing the skin surface (view not shown). The nonconductive sheet is advantageously a polyimide, however the composition of the non-conductive sheet need not be limited to this material. Other suitable nonconductive sheet materials include polycarbonates, polyurethanes, polyvinylchlorides, polybutylenes, vinyl, silastic, and polyethylene.

The electrodes 106 are advantageously fabricated using a subtraction technique for production of printed circuit boards. An image of electrodes and traces is first developed on a copper-plated KAPTON® brand (duPont) polyimide polymer sheet. A photoresist layer is applied over the image. After exposure to ultraviolet radiation, the copper surrounding the photoresist protected regions is etched away with a ferric chloride solution. The photoresist is removed with an organic solvent, such as acetone. Following masking of the copper traces, nickel is electroplated onto the copper electrode pads. Gold is then electroplated onto the nickel electroplate. A final KAPTON® polyimide layer is laminated over the traces. Following soldering of the connector and integrated circuit elements, the electrode assembly is complete.

To ensure non-reactivity with a sensor attachment system 300 (FIGS. 3A, 3B) or with a skin layer itself, the exposed surfaces of electrodes 106 are plated with gold in some embodiments according to the present invention. However, other conductive materials that do not readily react with skin are used in other embodiments according to the present invention. Such conductive materials include suitable metals, metal alloys, metal—metal salt combinations, and conductive polymers. Between the gold surfaces of electrodes 106 and underlying metal paste traces 112 is an interposed layer of nickel (not shown) to ensure adequate plating of the gold. Other interposed metal layers, e.g. tin, may be used. Opposite the gold-plated surface of the electrode the metal paste traces 114 in a Y-configuration provide stability and strength for the electrodes 106. The metal paste traces 112 extend from each electrode 106, through a stem 116 of the electrode array 100, 400, to attach to the instrumentation connector 122. The width and thickness of the metal paste traces 112 vary from 5–15 mil depending on the number of electrodes 106 in the array. In some embodiments according to the present invention, the metal paste traces 112 may be substituted with metallic inks, metallic wires, or conductive polymers.

FIG. 4 illustrates a second embodiment of the present invention in which integrated circuit elements are mounted on the instrumentation connector portion 120. The electrode array 400 in FIG. 4 is illustrated as 64 electrode two dimensional array, although any number of electrodes may be included in the array. The electrode array in FIG. 4 is operated by integrated circuit elements consisting of shift registers 470 and multiplexers 472 mounted on the instrumentation connector portion 120 of the electrode array 400. In the embodiment depicted in FIG. 4, there is one shift register 470 and four multiplexers 472, however other configurations are possible and are contemplated as being within the general scope of the present invention. Moreover, although the embodiment illustrates shift registers 470 and multiplexers 472 mounted separately from each other, those of skill in the art will appreciate that they may fabricated on the same integrated circuit chip. Those of skill in the art will also appreciate that additional circuitry, such as a control device, may also preferably be included with the shift registers 470 and multiplexers 472.

The shift registers 470 and mutiplexers 472 preferably cause individual electrode elements in the array to provide a sensing signal, such a voltage, in a time division manner according to a predetermined cycling frequency, as understood by those of skill in the art. Moreover, those of skill in the art will appreciate that the shift registers 470 and multiplexers 472 may be configured to sample the sensing signal from one electrode or from a plurality of electrodes at any given sampling time period. The sensing signals provided from the electrodes may then be provided to an analyzing device, such as a nerve location device, through instrumentation connector 122. Instrumentation connector 122 may be a plug type connector, or any other known type of electrical connector.

Figure 8:
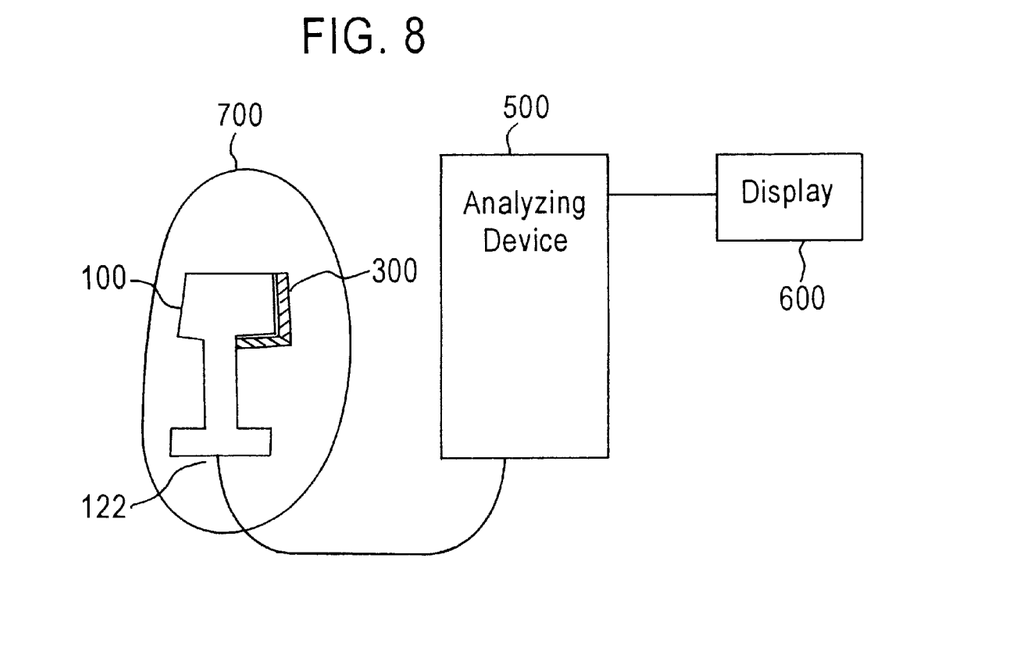
FIG. 8 illustrates the use of the present invention with an electronic measurement device, such as a nerve mapping device.

FIG. 8 illustrates the electrode array 100 joined with the sensor attachment system 300 and mounted on the skin of a subject 700. As illustrated in FIG. 8, the electrode array is connected to an analyzing device 500 via instrumentation connector 122. The analyzing device 500 preferably drives a display device 600 to display the results of the analysis performed by the analyzing device 500. In the preferred embodiment, the analyzing device 500 may be a nerve location device, which determines the location of nerves based on the signals received from the electrode array 100, as described in commonly owned U.S. Pat. No. 5,560,372 to Cory. However, the analyzing device 500 is not limited to a nerve location device, and may be any device configured to receive electrical sensing signals from a test organism. The analyzing device 500 and the display device 600 may be collectively referred to as a medical imaging instrument.

The electrode arrays 100, 400 are wide at both the electrode sensor region 130 and the instrumentation connector region 120. Between the instrumentation connector region 120 and the electrode sensor region 130, the stem region 116 is narrow to promote flexibility and convenience of use. The electrode sensor region 130 of the electrode array 100 preferably contains a registration hole 126 and a registration notch 128. These design characteristics allow for accurate positioning with the sensor attachment system 300. A tab 162 is on one side of the electrode sensor portion 130 of the electrode array 100 for ease of removal of the electrode array 100 from a skin marking guide 308 (FIG. 3B) after sampling is complete. In some embodiments according to the present invention, the electrode arrays 100, 400 have one registration hole 126 and registration notch 128. In other embodiments according to the present invention, the number and position of the registration notches 128 and registration holes 126 vary, depending upon the dimensions of the sensor portion 130 of the electrode array 100, 400. Some larger two-dimensional electrode arrays employ additional registration elements. Others require no registration notches 128 or registration holes 126.

The instrumentation connector portion 120 of the electrode array 100, 400 preferably has a plastic rigidizer 138 (which may made of any suitable material other than plastic) positioned on the side of the electrode array opposite the exposed electrodes. The rigidizer 138 provides additional support for the instrumentation connector 122 and any attached integrated circuit elements such as shift registers 470 and multiplexers 472. A return lead 134 connects via a soldered union 136 to a metal trace 132 running to the instrumentation connector 122. The instrumentation connector portion 120 of the electrode array 100, 400 is encapsulated in molded medicinal grade silicone polymer or polyethylene. In some embodiments according to the present invention, metal paste material is applied at points of curvature and stress on the electrode array 100, 400 to provide additional shear-resistance and prolong the useable life span of the electrode array.

Figure 2:
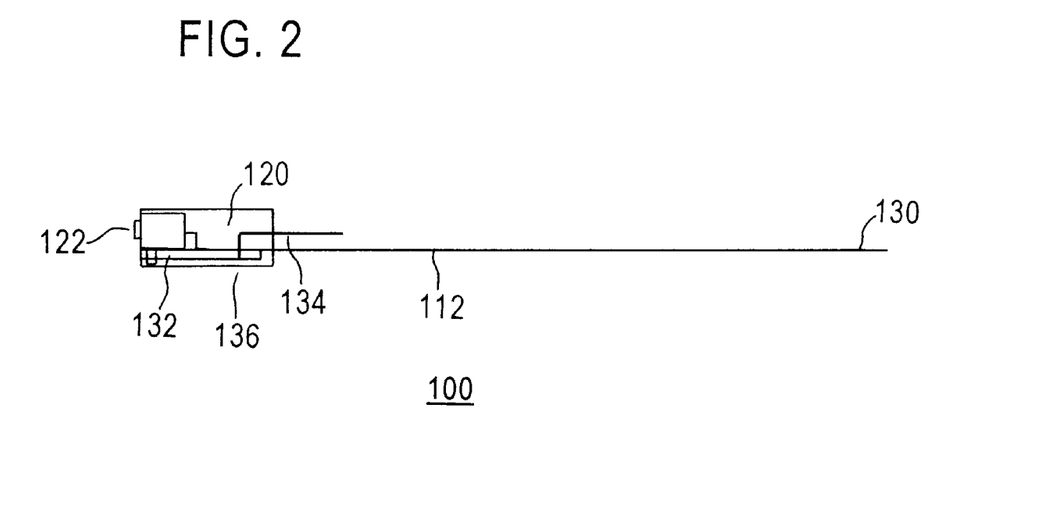
FIG. 2 is a cross-sectional side view of an electrode array of the present invention in a 16-electrode conformation.

FIG. 2 depicts a side cross-sectional view of the electrical components of the embodiment depicted in FIG. 1. Within the instrumentation connector region 120 is instrumentation connector 122, which connects to metal paste traces 112. The return electrode wire(s) 134 are connected to instrumentation connector 122 through metal paste trace 132 at soldered union 136. The metal paste traces 112 connect to the electrode sensor region 130.

The electrode array of the invention is preferably used in combination with a skin sensor attachment system as described herein. However, the electrode array can also be used independently of the skin sensor attachment system, for example, as a diagnostic device to screen peripheral nerves for abnormalities.

Figure 3A:
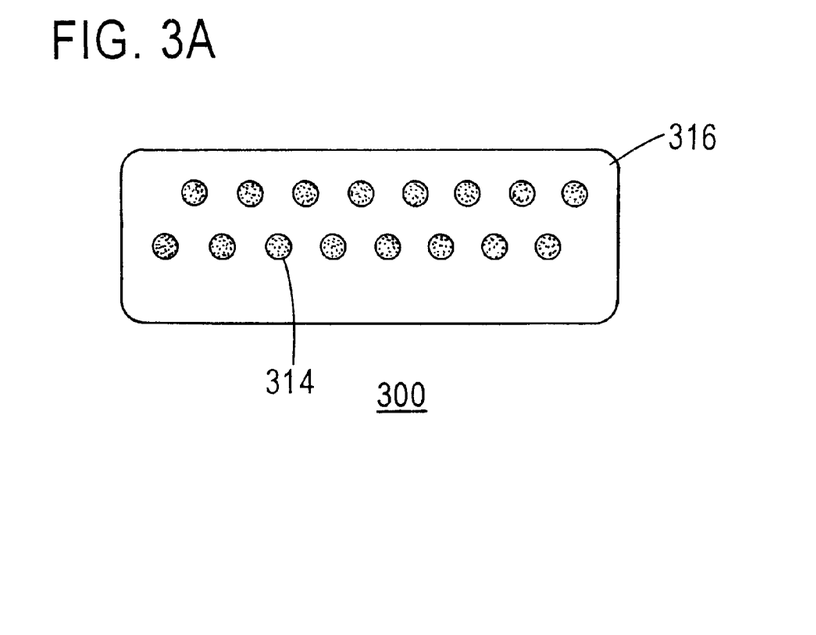
FIG. 3A shows a sensor attachment system in a 16-electrode conformation, top view.
Figure 3B:
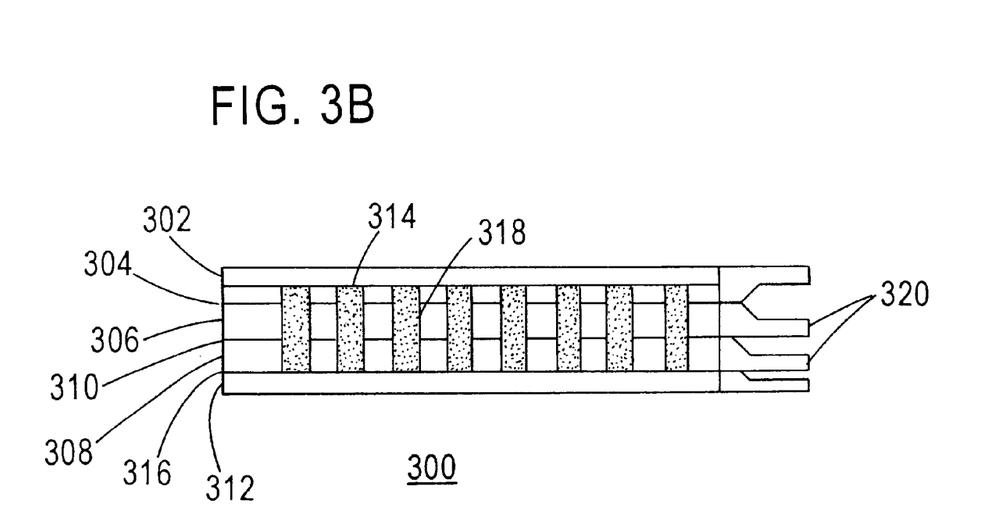
FIG. 3B shows a sensor attachment system in a 16-electrode conformation, side view.

Sensor attachment systems. An embodiment of a sensor attachment system 300 for use with an electrode array 100 as depicted in FIG. 1 is depicted in FIGS. 3A and 3B. Sensor attachment system 300 is shaped to conform exactly to a particular electrode array configuration such as electrode array 100 in FIG. 1. A suitable sensor attachment system 300 according to the present invention consists of seven layers:

1. Top cover 302 of the sensor attachment system 300 is preferably composed of polyethylene, polystyrene, polyvinylchloride, polybutylene, polyurethane or other material and provides protection for the underlying materials.
2. A top adhesive layer 304 allows solid connection of the sensor attachment system 300 with the electrode array 100. In the preferred embodiment, the top adhesive layer 304 does not extend over the conductor islands 314.
3. Beneath the top adhesive layer 304 is a support layer 306 comprised of, but not limited in composition to, closed-cell foam. The thickness of the support layer 306 may be varied depending on the application intended.
4. Between the support layer 306 and a skin marking guide 308 is an intermediate adhesive layer 310, which joins the support layer 306 and the skin marking guide 308.
5. The skin marking guide 308 is formed of a material such as 4 mil polyethylene, which is preferably colored so as to be easily visible on all skin types (e.g, blue or white).

6. A bottom adhesive layer 316 allows the skin marking guide 308, and thus the entire sensor attachment system with the electrode array 100 on top of it, to adhere to the skin of the subject. The skin marking guide 308 allows the skin to be marked at site(s) of interest before its removal.
7. Bottom cover 312 of the sensor attachment system 300 is preferably composed of polyethylene, polystyrene, polyvinylchloride, polybutylene, polyurethane or other material and provides protection for the underlying materials.

Holes 314 are formed through all layers of the sensor attachment system 300 except for the top cover 302 and the bottom cover 312. The holes 314 are filled with a conductive material 318 comprising, but not limited in composition to, an organic hydrogel. Registration elements are preferably positioned on the sensor attachment system to provide for accurate placement of the electrode array 100 on the sensor attachment system 300 and to indicate orientation on the nerve location device display. Tabs 320, aligned with the electrode array tab 162 of electrode array 100, are found on the support layer 306 and the skin marking guide 308. The tabs 320 aid in removal of the support layer 306 and skin marking guide 308. In some embodiments, the sensor attachment system 300 may be packaged in a rigid container or aluminized pouch (not shown) which is sealed in an airtight fashion. The sensor attachment system 300, in its container, is preferably capable of withstanding sterilization by gamma-irradiation. In its sealed container, the sensor attachment system 300 preferably has a shelf life of approximately 18 months.

Figure 5A:
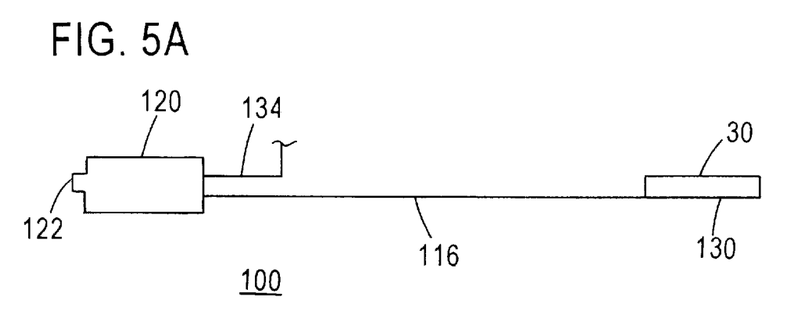
FIG. 5A shows an assembly of an electrode array and a sensor attachment system according the present invention, side view.
Figure 5B:
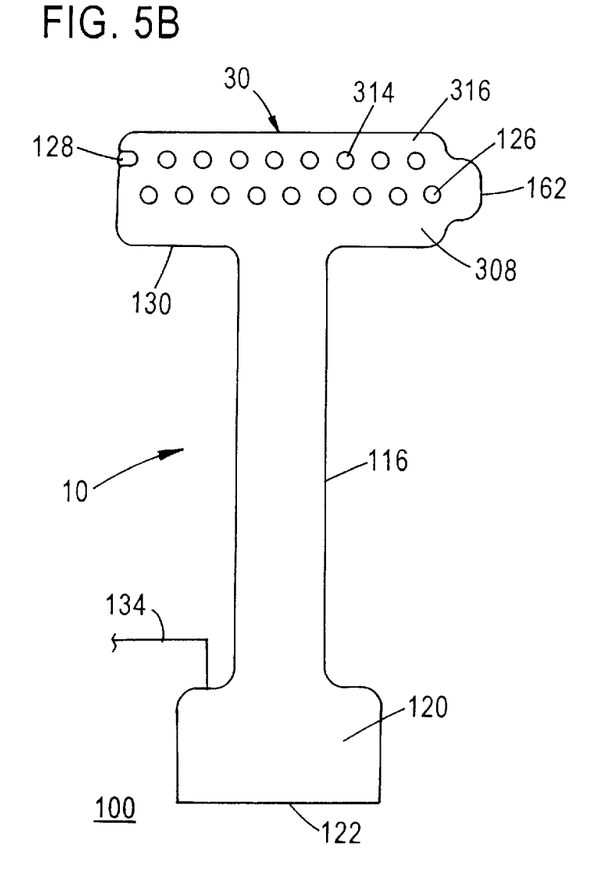
FIG. 5B shows an assembly of an electrode array and sensor attachment system of FIG. 5A, view from the sensor attachment side.

A combination of sensor attachment system 300 and electrode array 100 is shown in FIGS. 5A and 5B. In FIG. 5A sensor attachment system 300 is applied to electrode sensor region 130 of electrode array 100. In FIG. 5B, the electrode array 100 and sensor attachment system 300 are seen from the side facing the skin during attachment. The sensor attachment system 300 is seen after bottom cover 312 has been peeled off. Visible are registration notch 128, registration hole 126, tab 162, conductor islands 314 and adhesive layer 316, which covers skin marking guide 308. Return lead 134 connects to instrumentation connector region 120, which has an instrumentation connector 122 for connection to an appropriate instrument.

An electrode array and sensor attachment system according to the present invention, when connected to an appropriate nerve location device, may be used to identify peripheral nerves, neuromas, myofascial trigger points, nerve entrapments, and acupuncture points. To use the invention, one preferably attaches the sensor attachment system 300 to an appropriately configured electrode array 100, which is then connected to the nerve location device. When used for sensing nerves, the electrode array may preferably operate in the same manner as the electrode array described in commonly owned U.S. Pat. No. 5,560,372. Particularly, with reference to FIG. 10(A), an input current may be applied to each electrode, then, as shown in FIG. 10(B) an output voltage is sensed from each electrode. The variations in the output voltage received indicate the underlying tissue electrical conductance.

Figure 6:
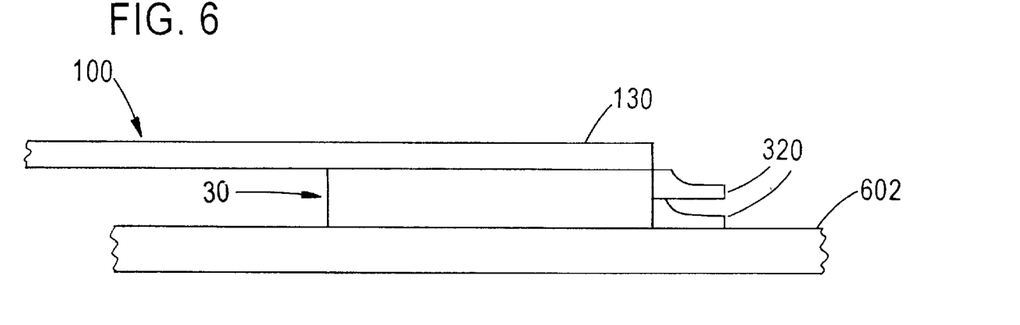
FIG. 6 shows a side view of an electrode array and sensor attachment system according to the present invention attached to an area of skin.

FIG. 6 depicts an embodiment according to the present invention, wherein the sensor attachment system 300 is then attached to skin 602. Electrode array 100 has been attached to the sensor attachment system 300, from which top layer 302 and bottom layer 312 have been removed.

Figure 7A:
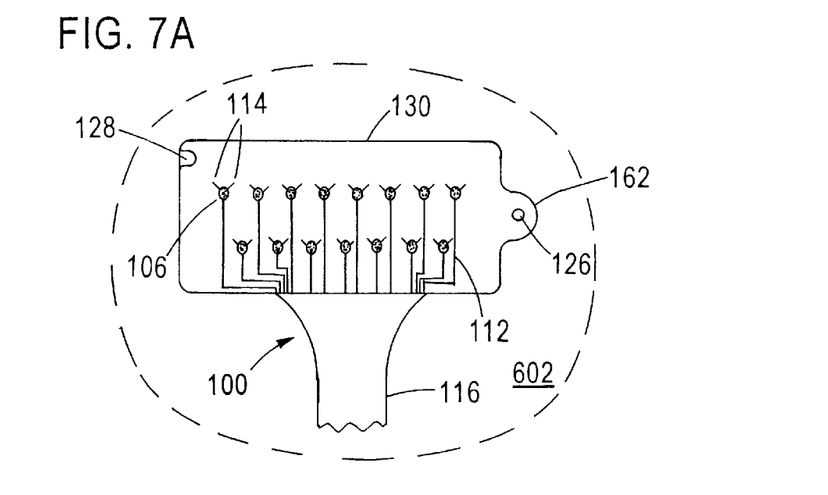
FIGS. 7A–7D illustrate the steps of removing an electrode array from a skin marking guide according to the present invention, marking a location on an area of skin through a hole in the skin marking guide, and removal of the skin marking guide from the area of skin.

A method of using the electrode array 100 and sensor attachment system 300 according to the present invention is depicted in FIGS. 7A–7D. In FIG. 7A, an electrode array 100 is shown as it is attached to skin 602 through a sensor attachment system (not shown). Visible in this view is the electrode sensor region 130 of the electrode array 100, which comprises electrodes 106, metal paste traces 112 and 114, registration notch 128, registration hole 126 and tab 162. The electrode sensor region 130 is attached to the instrumentation connector region (not shown) through stem 116.

Figure 7B:
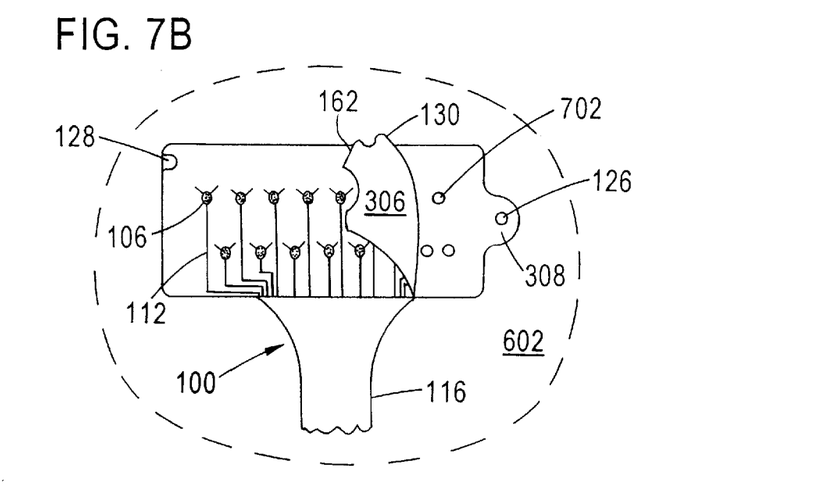

FIG. 7B depicts removal of electrode array 100 from skin marking guide 308. The support layer 306 goes with electrode array 100 as it is peeled back from the skin marking guide 308 via tab 162.

Figure 7C:
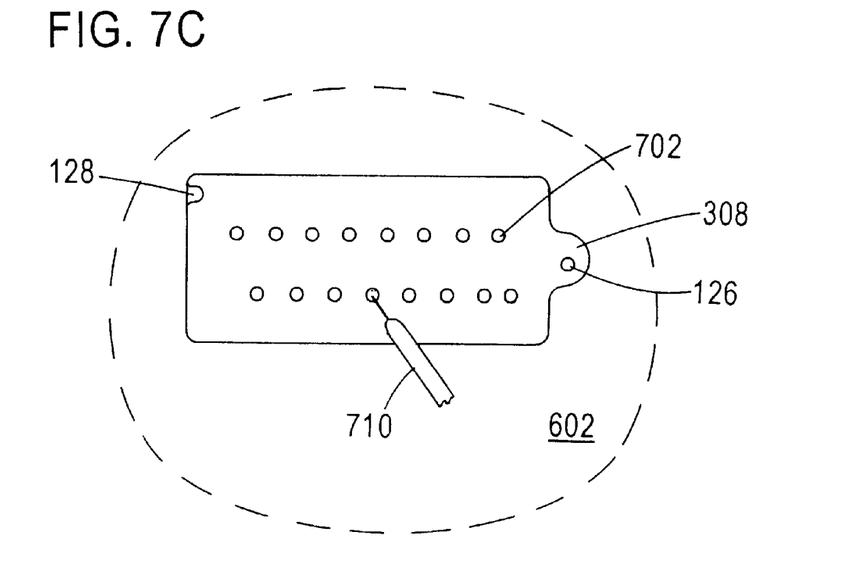

FIG. 7C depicts marking of skin 602 through a hole 702 in skin marking guide 308 with a pen 710.

Figure 7D:
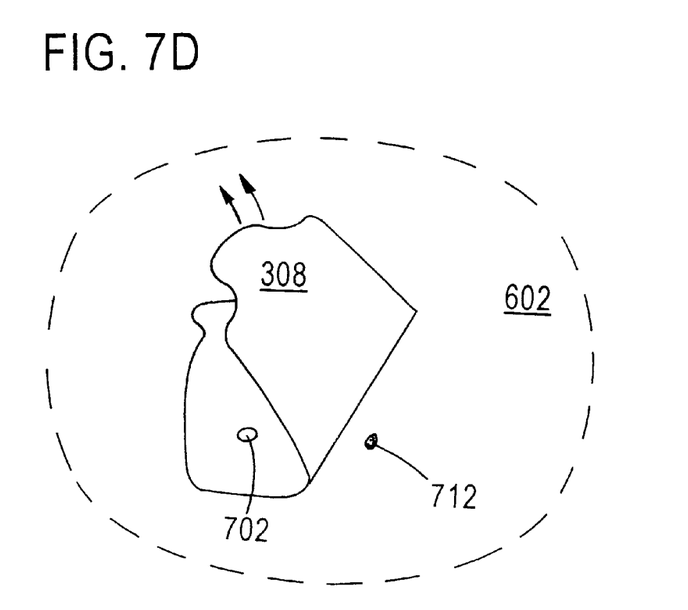

FIG. 7D depicts peeling away of skin marking guide 308 from skin 602 to reveal mark 712.

Steps for carrying out a method of using an electrode array and sensor attachment system according to the present invention include the following.

1. Connect the electrode array 100 to an instrumentation connector (not shown) of a nerve location device.
2. Remove the top cover 302 from the electrode array side of the sensor attachment system 300.
3. Align the registration features of sensor attachment system 300 with the registration notch 128 and the registration hole 126 of electrode array 100, position and securely attach the sensor attachment system 300 to the electrode array 100.
4. Remove bottom cover 312 from skin surface side of the sensor attachment system 300.
5. Attach the skin marking guide 308, now on the combined electrode array and sensor attachment system, to intact skin of a suitable subject. The skin is advantageously prepared by stripping 3–5 times with adhesive tape.
6. Attach the return electrode(s) (for example, a standard ECG electrode) (not shown) to the skin of subject within 10–20 cm of the electrode array assembly 100.
7. Attach the return electrode wire(s) 134, for instance with an alligator clip, to the return electrode(s) of the instrument (not shown).
8. Obtain samples with the nerve location instrument (not shown).
9. Once skin surface has been sampled with the nerve location device, there are two options:
    a. Using the tab 162 on the electrode array 100 and the tab(s) 320 on the sensor attachment system 300, remove the entire electrode array 100 and the sensor attachment system 300 from skin surface, or
    b. Using the tabs 320 on the sensor attachment system 300 as an aid, remove all but the skin marking guide 308 from the skin surface. At this point, one may mark the skin through the skin marking guide 308 at the point(s) of interest determined by the nerve location device. Once the skin surface has been marked, the skin marking guide 308 is removed and the skin surface prepared for positioning of a nerve stimulation needle and/or a needle for therapeutic injection (e.g., regional anesthesia or pain relief).
10. All portions of the sensor attachment system 300 are discarded.
11. The electrode array 100 is discarded, if in a disposable embodiment, or if in a reusable embodiment, is cleansed with isopropyl alcohol or, if desired, may be sterilized under ethylene oxide, gamma radiation, or autoclaving. The latter method may decrease the longevity of the electrode array.

While the foregoing preferred embodiments serve to illustrate the present invention and the best mode of operation thereof, other suitable embodiments, arrangements and uses may be envisioned by the ordinary artisan and as such are contemplated as being within the scope of the herein described invention.

What is claimed is:

1. A method of using a sensor system comprising a sensor attachment system, an electrode array, a return lead, and a medical imaging instrument, comprising the steps of:
   connecting the electrode array to a medical imaging instrument;
   lining up registration features contained on the sensor attachment system with registration features contained on the electrode array and connecting the sensor attachment system to the electrode array;
   attaching the sensor attachment system to skin;
   attaching the return lead to skin.

2. A method of using a sensor system comprising
   comprising an electrode array and a medical imaging instrument, said electrode array comprising:
   a sheet of electrically non-conductive material having a sensor electrode region, an instrumentation connector region and a flexible stem region mechanically joining the sensor electrode region and the instrumentation connector region;
   circuitry comprising an electrode array having one or more electrodes, which are disposed within the sensor electrode region,
   at least one connection lead, each connection lead corresponding to at least one electrode disposed within the instrumentation connector region, and
   at least one return lead disposed within the instrumentation connector region, each return lead corresponding to an electrode and a connection lead, and being operable to connect said connection lead with the corresponding electrode, comprising the steps of:
   connecting the electrode array to a medical imaging instrument;
   coating each electrode with an electrically conductive aqueous gel;
   placing the electrode array on a body surface; and
   attaching the return lead(s) to skin.

3. A sensor system for the imaging of peripheral nerves, comprising a sensor attachment system and an electrode array and a medical imaging instrument,
   said sensor attachment system comprising:
   at least one registration feature for alignment of the sensor attachment system with an electrode array,
   a skin marking guide layer, having at least one marking hole therein;
   a support layer having one conductor island hole corresponding to each marking hole in the skin marking guide layer, each said conductor island hole containing a conductor island, which projects into its corresponding marking hole;
   wherein the skin marking guide layer and the support layer are detachably affixed one to the other; and
   said electrode array comprising:
   a sheet of electrically non-conductive material having a sensor electrode region, an instrumentation connector region and a flexible stem region mechanically joining the sensor electrode region and the instrumentation connector region;
   circuitry comprising an electrode array having one or more electrodes, which are disposed within the sensor electrode region,
   at least one connection lead, each connection lead corresponding to at least one electrode disposed within the instrumentation connector region,
   at least one return lead disposed within the instrumentation connector region, each return lead corresponding to an electrode and a connection lead, and operable to connect said connection lead with the corresponding electrode,
   an electrically conductive connection between each electrode and its corresponding connection lead,
   registration features on the sensor electrode region for alignment with a sensor attachment system.

4. The sensor system of claim 3, wherein the registration feature may be a hole, notch, mark, shape or colored region.

5. The sensor system of claim 4, wherein the skin marking guide layer comprises at least one of polyurethane, polyethylene, polypropylene, polyvinyl chloride, and copolymers thereof.

6. The sensor system of claim 3, wherein the support layer is comprised of at least one of polyethylene, polypropylene, polyurethane, polyvinyl chloride, silastic and copolymers thereof.

7. The sensor system of claim 3, wherein the support layer is comprised of a closed-cell foam.

8. The sensor system of claim 3, wherein the support layer is comprised of an open-cell foam.

9. The sensor system of claim 3, wherein the conductor island is comprised of at least one of silver—silver chloride gel or hydrogel.

10. The sensor system of claim 3, wherein the sheet of electrically non-conductive material comprises at least one of polyimide, vinyl, polyvinyl chloride, silastic, polyethylene, polyurethane and polycarbonate.

11. The sensor system of claim 3, wherein the electrodes contain at least one of a gold-plating, nickel-plating, platinum, palladium, metal—metal salt combinations including silver—silver chloride, or a conductive polymer.

12. The sensor system of claim 3, wherein the electrodes are connected to the connection leads by at least one of metal paste conductive traces, metallic ink metallic wire, and conductive polymer.

13. The sensor system of claim 3, wherein each connection lead corresponds to only one electrode disposed within the instrumentation connector region.

14. The sensor system of claim 3, further comprising integrated circuitry chips connected to the connection leads and being operable to connect a plurality of connection leads to a single connection lead.

15. The sensor system of claim 3, wherein said electrodes are supported by metal paste reinforcement.

16. The sensor system of claim 3, wherein said return lead corresponds to a return electrode disposed within the sensor electrode region of the electrode array.

17. The sensor system of claim 3, wherein said return lead corresponds to a return electrode that is separated from the sensor electrode region of the electrode array.

18. The sensor system of claim 3, wherein said return lead corresponds to a return electrode that is separate from the electrode sensor region of the electrode array, and said electrode is comprised of at least one of a hydro gel-containing electrode, a silver—silver chloride gel electrode, a cup electrode that is filled with conductive gel, or a needle electrode.

* * * * *